United States Patent
Sorensen et al.

(10) Patent No.: US 12,011,470 B2
(45) Date of Patent: Jun. 18, 2024

(54) MICELLE PREPARATIONS OF FULL-SPECTRUM HEMP OIL

(71) Applicants: Clint Sorensen, St. George, UT (US); Melanie Montgomery, Scottsdale, AZ (US); Matt Smith, Highland, UT (US)

(72) Inventors: Clint Sorensen, St. George, UT (US); Melanie Montgomery, Scottsdale, AZ (US); Matt Smith, Highland, UT (US)

( * ) Notice: Subject to any disclaimer, the term of this patent is extended or adjusted under 35 U.S.C. 154(b) by 0 days.

(21) Appl. No.: 17/711,014

(22) Filed: Mar. 31, 2022

(65) Prior Publication Data

US 2023/0038771 A1 Feb. 9, 2023

Related U.S. Application Data

(63) Continuation of application No. 17/388,061, filed on Jul. 29, 2021, now abandoned, which is a continuation of application No. PCT/US2021/071038, filed on Jul. 28, 2021.

(51) Int. Cl.
| | |
|---|---|
| *A61K 36/185* | (2006.01) |
| *A61K 9/00* | (2006.01) |
| *A61K 9/107* | (2006.01) |
| *A61K 31/05* | (2006.01) |
| *A61K 31/352* | (2006.01) |
| *A61P 25/20* | (2006.01) |

(52) U.S. Cl.
CPC .......... *A61K 36/185* (2013.01); *A61K 9/0053* (2013.01); *A61K 9/1075* (2013.01); *A61K 31/05* (2013.01); *A61K 31/352* (2013.01); *A61P 25/20* (2018.01)

(58) Field of Classification Search
CPC ..... A61P 25/20; A61K 9/0053; A61K 9/1075; A61K 31/05
See application file for complete search history.

(56) References Cited

U.S. PATENT DOCUMENTS

| | | |
|---|---|---|
| 10,052,303 B2 | 8/2018 | Winnicki |
| 10,709,748 B2 | 7/2020 | Witowski |
| 2019/0216869 A1 | 7/2019 | Salm et al. |

FOREIGN PATENT DOCUMENTS

| | | |
|---|---|---|
| WO | WO 2013/009928 | 1/2013 |
| WO | WO2013076471 | 5/2013 |
| WO | WO 2015/068052 | 5/2015 |
| WO | WO2015068052 | 5/2015 |
| WO | WO 2020/150616 | 7/2020 |
| WO | WO 2017/147691 | 9/2020 |

OTHER PUBLICATIONS

Epidolex (R) prescribing information. Greenwich Biosciences Inc. 2020.
Cannabis compounds exhibit anti-inflammatory activity in vitro in COVID-19-related inflammation. SM Anil et al., Sci Rep . Jan. 14, 2021;11(1):1462.
The plant cannabinoid Delta9-tetrahydrocannabivarin can decrease signs of inflammation and inflammatory pain in mice. D Bolognini et al., r J Pharmacol. Jun. 2010;160(3):677-87.
Cannabinoids block cell ular entry of SARS-CoV2 and the emerging variants. RB van Breeman et al., J. Natural Products, Oct. 3, 2021.
Opportunities, Challenges and Pitfalls of Using Cannabidiol as an Adjuvant Drug in COVID-19. B. Malinowska et al., Int J Mol Sci . Feb. 17, 2021;22(4):1986.
Towards Better Delivery of Cannabidiol (CBD). SA Millar et al., Pharmaceuticals (Basel) . Aug. 28, 2020;13(9):219.
Cannabidiol Inhibits SARS-CoV-2 Replication and Promotes the Host Innate Immune Response. NC Nguyen et al., bioRxiv. Mar. 10, 2021;2021.03.10.432967.
Cannabidiol in Anxiety and Sleep: A Large Case Series. S Shannon et al., Perm J. 2019;23:18-041.
Cytokine storm in COVID-19: pathogenesis and overview of anti-inflammatory agents used in treatment. Soy M Keser et al., Clin Rheumatol. Jul. 2020;39(7):2085-2094.
Cannabidiol for viral disease. AM Tagne et al., Cannabis Cannabinoid Res 5(2), 2020.
Dental anxyety management by full spectrum CBD formulations. DL Cooper et al., Clinics in medicine, 3(1038), 034, 2021.
Anti-inflammatory activity of a full spsectrum CBD rich hemp formulation in patients with COVID-19 infection. M Montgomery et al., Clinics in Medicine 4(1042), 016, 2022.
Efficacy and Safety of Cannabidiol and Tetrahydrocannabivarin on Glycemic and Lipid Parameters in Patients With Type 2 Diabetes. KA Jadoon, Diabetes Care. Oct. 2016;39 (10):17.
PCT/US2021/071038 International search report and written opinion, IP Australia, dated Oct. 28, 2021.
PCT/US2021/071038 Article 34 amendment and response, dated May 31, 2022.
PCT/US2021/071038 (corresponding PCT application): Corrected International Preliminary Report on Patentability (IPRP), dated Jan. 24, 2023.
"Bioavailability Study Purzorb® Full Spectrum CBD Oil Human Subjects Trial—Apr. 2018" Date document created Jan. 5, 2019 (IPRP ref. D6).
"Understanding CBD oil bioavailability, metabolism and water solubility" Date document created Feb. 20, 2020 (IPRP ref. D7).

*Primary Examiner* — Marcos L Sznaidman
(74) *Attorney, Agent, or Firm* — MS IP Law (57) ABSTRACT

This disclosure provides cannabinoid preparations for human consumption that have proven clinical benefits. The preparations are made from full-spectrum hemp oil, which includes a mixture of cannabinoids that work synergistically to achieve the beneficial effects. The hemp oil is micellized, which increases intestinal absorption, resulting in higher potency and a more rapid onset of action. The micellized oil may be combined with micellized cinnamon or clove oil as a flavor enhancer. When consumed daily, the combination of using full spectrum hemp oil with micellization imparts the consumer with an improvement in well-being by several criteria. Benefits include a reduction in inflammatory cytokines, lowering in glucose levels, and weight loss. The micellized cannabinoid preparations of this invention improves sleep quality by extending the period of time spent in deep sleep.

11 Claims, 8 Drawing Sheets

MICELLE PREPARATIONS OF FULL-SPECTRUM HEMP OIL

FIELD OF THE INVENTION

This disclosure relates to the management of sleep quality in patients with COVID-19 and other viral infections. It explains how to lower cytokine levels and improve time spent in deep sleep using a micellized preparation of a special blend of cannabinoids from hemp oil

BACKGROUND

Industrial hemp is a variety of the *Cannabis sativa* plant species that is grown specifically for the industrial uses of its derived products. Commercially, it has been refined into paper, textiles, clothing, biodegradable plastics, paint, insulation, biofuel, food, cosmetics, nutritional supplements, and animal feed. Although industrial hemp and the cannabis drug marijuana are both members of the *Cannabis sativa* species, they have distinctive biochemical compositions and uses.

Unique to industrial hemp is a high amount of phytocannabinoids, especially cannabidiol. CBD is a 21-carbon terpenophenolic compound which is formed following decarboxylation from a cannabidiolic acid precursor. In contrast to trans-$\Delta^9$-tetrahydrocannabinol (THC), CBD is non-intoxicating, but exerts a number of beneficial pharmacological effects. At lower doses, CBD helps promote and maintain health, including antioxidative, anti-inflammatory, and neuroprotection effects.

Preparation and use of cannabinoid micelles and formulations is put forth, for example, in U.S. Pat. Nos. 8,808,734, 9,839,612, 10,258,601, 10,456,357, and 10,568,865, and in pre-grant publications US 2019/0183853 A1 and US 2020/0061138 A1. Use of a cannabinoid as an antioxidant or neuroprotectant is put forth in U.S. Pat. No. 6,630,507. Commercially available products for human consumption containing CBD or hemp oil (sometimes in the form of micelles) can be obtained from several commercial sources, including Virun Nutra Biosciences (Nuriv), IQ Labs, Iberoptima, Kazmira, and Enhanced CBD Health.

Nabiximols (brand name Sativex®) is essentially an aerosolized mist for oral administration containing a near 1:1 ratio of CBD and THC. Also included are minor cannabinoids and terpenoids, ethanol and propylene glycol excipients, and peppermint flavoring. The drug is made by GW Pharmaceuticals, and has been approved in 25 countries for treatment of cancer pain. The CBD drug Epidiolex® (from Greenwich Biosciences) has been approved by the Food and Drug Administration in the U.S. for treatment of two rare and severe forms of epilepsy. Compositions containing full spectrum hemp oil and cinnamon are proposed in U.S. Pat. No. 10,542,770 and marketed in the U.S., for example, by Young Living Essential Oils, Edens Herbals, and Kushly Corp. Compositions containing full spectrum hemp oil and clove flavoring are proposed in pre-grant publications US 20190247325 A1, US 2020/0146984 A1, and US 20200230185 A1 and marketed in the U.S., for example, by Healthy Hemp Oil, Leafwise Naturals, and Apple CBD Plus.

An article by Bolognini et al. (Br. J. Pharmcol. (2010) 160, 677-687) reviews the use of THC to decrease signs of inflammation and inflammatory pain in mice. International patent application WO 2013/076471 proposes the use of tetrahydrocannabivarin (THCV) for use in the protection of pancreatic islet cells. Jadoon et al. (Diabetes Care (2016) 39, 1777-1786) discuss a clinical trial to assess the efficacy and safety of CBD and THCV on glycemic and lipid parameters in patients with Type 2 diabetes. J. Tietelbaum (Altern Ther Health Med. 2019 Jun;25(S2):21-23) has published a review of hemp oil, CBD, and marijuana as powerful pain, insomnia, and anxiety-relieving modalities.

The team at WSMEF Technology has been manufacturing and marketing bio-absorbable ingredients from hemp oil and formulating them into products for about six years. Purzorb® is a trademark registered in 2016 that is used in conjunction with a mixture of oil based hemp products that are absorbable or bioavailable to the body. In laboratory studies, Purzorb® formulated Hemp CBD Oil has demonstrated significantly more bioavailability than unformulated hemp. Products from this process are marketed by the entity Med 7 (customercare@ Med 7cbd.com) and Pur7 (purseven.com) under the trade name Hempzorb81™. The CBD in these products is 85% bio-absorbable with an onset of action of 15 minutes, which makes it 640% more efficient and seven times faster than regular CBD oil. Certain products from Med 7 also contain other naturally occurring phytocannabinoids, terpenes and flavonoids that promote the effects of CBD in vivo. Products from Med 7 meet or exceed FDA regulations including THC content of less than 0.3% US, 0.2% EU, and are U.S. Farm Bill compliant.

Aspects of the technology described in this disclosure are licensed to PurHealthRX and Med 7 from WSMEF LLC, the named applicant for this patent disclosure and owner of the invention claimed below.

SUMMARY

This disclosure provides cannabinoid preparations for human consumption that have proven clinical benefits. The preparations are made from full-spectrum hemp oil, which includes a mixture of cannabinoids that work synergistically. The hemp oil is micellized, which considerably increases intestinal absorption, resulting in higher potency and a more rapid onset of action. The micellized oil may be combined with micellized cinnamon or clove oil as a flavor enhancer.

When consumed daily, the combination of full spectrum hemp oil with the micellization imparts the consumer with an improvement in well-being in several dimensions. Benefits include a reduction in inflammatory cytokines, which can decrease joint pain and reduce the risk of cytokine storm in patients infected with the virus that causes COVID-19. In subjects with Type II diabetes, the preparation causes a beneficial lowering in average glucose levels, shown by a decreased level of circulating glycated hemoglobin (HbA1c). The micellized cannabinoid preparations of this invention also improve sleep quality by extending the period of time spent in deep sleep.

Treating COVID-19 and Other Conditions using Micellized Full Spectrum Hemp Oil

The cannabinoid containing compositions put forth in this disclosure can be used for improving well-being of a subject in a number of ways. The subject is administered with a course of therapy that includes oral consumption of a cannabinoid preparation daily or periodically for a time period that is usually at least a week, more typically two, three, or four weeks or more, or about 20 days. The preparations are usually given once a day, although multiple doses per day and/or skipped days are permissible. The cannabinoids contained in the preparation consist essentially of micelles suspended in an aqueous solvent, wherein the micelles in the preparation comprise one or more amphipathic compounds or surfactants combined with full-spectrum hemp oil. The hemp oil is a mixture of cannabinoids, and the resulting preparation and cannabinoid content thereof is also a mixture.

One beneficial effect of regular consumption is that it decreases circulating levels of inflammatory markers such as tumor necrosis factor alpha (TNFα) and interleukin 6 (IL-6) by as much as 25 to 50% or more. Also reduced are markers that indicate the presence of ongoing inflammation, such as C reactive protein (CRP) and/or erythrocyte sedimentation rate (EST) by as much as 10 to 25% or more. Other cytokines and markers of inflammation are also reduced, as described below. The effectiveness of the therapy can be assessed by subjective and/or objective assessments of signs and symptoms often associated with the condition being treated, and/or by following levels of these markers in the circulation: for example, on a weekly basis for several weeks, typically starting shortly following the diagnosis.

Minimizing inflammation in turn has several benefits. Besides helping the treated subject feel better, it may decrease the severity of a viral, bacterial, or parasitic infection. Data is presented below from a clinical trial of patents infected with SARS-CoV-2 (the virus that causes COVID-19). The data indicate that regular administration of a micellized preparation of full spectrum hemp oil is effective in reducing the circulating levels of cytokines and inflammatory markers by a comparable amount in subjects who have symptoms and/or signs of infection. Such signs and symptoms include the clinical manifestation of COVID-19 (respiratory distress, cough, loss of smell, and so on), and/or a positive virus antigen test. Lowering cytokine levels will decrease the degree of inflammation in the subject and/or reduce the risk of further complications due to cytokine storm. Other benefits for COVID-19 patients may be to inhibit replication of the virus, and inhibit development of severe respiratory distress syndrome (SARS). The cannabinoid preparations may be equally effective in subjects infected with another corona virus, or with another class of virus such as an influenza. When used as a treatment of an infection, the cannabinoid preparation may be part of a therapy in combination with other treatment agents: such as a pathogen specific vaccine, with passive antibody, small-molecule antiviral compounds, and general supportive care.

Clinical data presented below shows that minimizing inflammation with the micellized full spectrum hemp oil is beneficial in resolving symptoms of inflammation in many clinical contexts, including autoimmune disease. in particular, the preparations considerably reduce joint pain in affected patients, moving the affected patients from a category that reflects moderate pain and a 20% decrease in movement to a category reflecting no pain. The placebo did not. The study group also had an improvement in the ratio of HDL/LDL from 0.27 to 0.31 (10 to 20%), reflecting improved lipid health. The use of the preparations of this invention to improve the welfare of patients affected by senescence related diseases of various manifestations is encouraged.

Another senescence related disease that benefits for administration with the cannabinoid preparations of this invention is Type II diabetes. Clinical data is also presented in this disclosure from an extensive human clinical trial in which various possible effects on patients having Type II diabetes were determined. Regular dosing for two to four weeks or more, or on an ongoing basis lowers circulating glucose levels (measured either when fasting or as part of a glucose tolerance test), and the circulating level of glycated hemoglobin (HbA1c) during or after administration of the course of therapy. The success of therapy can be monitored the sequelae of diabetes experienced by the treated subject, and the circulating level of HbA1c periodically or upon follow-up. A reduction of at least 10%, 20%, or 30% in circulating HbA1c can be achieved after 180 days of treatment. This is associated with a reduction in systolic blood pressure by about 10 psi, a reduction in weight by 10 pounds or more, and a reduction in girth by 5 to 10 percent.

Data from another clinical study presented below shows that regular dosing with a cannabinoid preparation put forth in this disclosure can improve sleep quality. The data indicate that the amount or proportion of a night's sleep of a subject that is spent in deep sleep by at least 30 minutes to an hour or more. Sleep latency is deceased by about 10 minutes, and the amount or proportion of time spent in REM sleep is also increased by about 10 minutes.

Other benefits of the micellized cannabinoid preparations in this disclosure can be an improvement in a mood disorder such as anxiety or depression.

The quality of a preparation that contains full-spectrum hemp oil in the form of micelles can be determined by measuring the effectiveness of the preparation in treating any of these conditions, alone or in combination. First, the preparation is administered to a population of human subjects orally on a periodic or daily basis for a suitable period, such as 20 days. The subjects are then assessed for their response for any combination of two, three, four, or more than four effects of interest to the investigator: for example, determining whether the subject experiences less joint pain following the treatment; measuring whether serum markers of inflammation have decreased in the subject following the treatment; measuring whether average circulating glucose levels in the subject have improved following the treatment; determining whether the subject has less anxiety using a subjective mood rating scale; s=determining whether there is an improvement in lipid health (for example, by circulating levels of HDL/LDL); and/or determining whether there is an improvement in sleep quality (for example, by the amount of a night's sleep spent in deep sleep). This can include measuring two or more serum markers of inflammation, such as C-reactive protein (CRP), tumor necrosis factor alpha (TNFα), interleukin 6 (IL-6), and erythrocyte sedimentation rate (EST).

Instead of or besides the clinical benefits determined from human testing, the quality of a preparation can be assessed by whether the preparation of micelles has both an onset of action and a potency in a consumer that is substantially enhanced (at least 2, 4, or 7-fold better) than a standard preparation of CBD oil). These parameters can be assessed directly, or by measuring an increase in the rate of absorption of cannabinoids in the preparation from the gastrointestinal tract of the consumer into the circulation. Ideally, the combined mixture of cannabinoids will total a cannabinoid content in the entire preparation of 0.1%, 0.3%, 0.5%, or 1.0% by weight, or a range of 0.05% to 1% or 0.1% to 0.5%. In terms of cannabinoids in the mixture, the cannabinoid content of the preparation comprises at least 70% cannabidiol (CBD). The cannabinoid content of the preparation comprises at least 2% tetrahydrocannabivarin (THCV). The cannabinoid content of the preparation may comprise at least 5% cannabidivarin (CBDV). and/or at least 2% cannabigerol (CBG). To satisfy local regulatory requirements, the level of tetrahydrocannabinolic acid (THC) may be no more than 1%, 0.3%, or 0.1%. by weight. The onset of action may occur 15 or 25 minutes following oral consumption, attributable to absorption of 70%, 85% or more of the active ingredients into the gastrointestinal tract within the first hour, whereby 25% to 50% or more of the cannabinoids reach the circulation within 6 hours. Both the potency (percent plasma blood levels) and the onset of action (minutes) is typically better by 4-fold, 7-fold, or more, compared with standard CBD preparations that haven't been micellized in the fashion described here.

This disclosure also provides pharmacological or therapeutic compositions of full spectrum hemp oil formulated for oral administration to a human subject. Because of the benefits of the multiple contents of full spectrum hemp oil, the compositions often includes the following components: a cannabinoid content of 0.1 to 1.0% by weight of the preparation, wherein the cannabinoid content consists essentially of micelles having a diameter of 10 to 100 microns, wherein the cannabinoid content contains the following components: at least 70% cannabidiol (CBD), at least 2% tetrahydrocannabivarin (THCV), at least 5% cannabidivarin (CBDV), and less than 1% Δ9-tetrahydrocannabinolic acid (THC), or other suitable ratio put forth below. Optionally, the compositions include a cinnamon oil and/or clove oil flavoring, each at a concentration of at least 1% by weight of the preparation, often but not necessarily in micelle form.

The reader is cautioned that the presence and proportions of minor cannabinoids in the full spectrum hemp oil used to make the preparation, the size and composition if the micelles, and the presence of other additives such as flavorings and preservatives should be selected, adjusted, and tested to have the desired effect: either in lowering average blood glucose level or circulating HbA1c (effectively treating Type II diabetes), decreasing joint pain, decreasing circulating TNF and IL-6 levels, improving HDL/LDL ratio, improving sleep quality, and/or increasing the amount of a night's sleep of a subject that is spent in deep sleep by at least 30 minutes. Sleep promoting preparations may optionally include other components that promote sleep, such as melatonin and herb extracts, such as valerian and/or skullcap.

The preparations are made by obtaining a preparation of full-spectrum hemp oil having an effective ration of cannabinoids (for example, a cannabinoid content of at least 70% cannabidiol (CBD), at least 2% tetrahydrocannabivarin (THCV), at least 5% cannabidivarin (CBDV), and less than 1% Δ9-tetrahydrocannabinolic acid (THC). The oil preparation is dissolved in an amphipathic solvent or surfactant as explained below, and then mixed or injected into an aqueous environment, thereby generating an aqueous suspension that constitutes the therapeutic preparation. The hemp oil preparation, the water-miscible organic solvent, the aqueous environment, and the mode of injection are all selected or adjusted to achieve the desired final composition: for example, in which at least 80% of the cannabinoids in the suspension are in the form of micelles having a diameter of 10 to 100 mm, and/or to achieve the desired clinical effects.

The micellized preparations of full spectrum hemp oil described below can be used for reducing circulating levels of inflammatory cytokines to improve the well-being of a subject, in the treatment of an inflammatory or infectious disease, in the treatment of inflammation or joint pain, in the treatment of infection by a SARS-CoV-2 virus, in the treatment of anxiety or other mood disorder, in the treatment of hypercholesterolemia, in the treatment of a sleep disorder, to improve sleep quality—or for any other effect referred to in this disclosure or which is otherwise desired by the reader.

Other aspects and embodiments of the invention are described in the sections that follow, the accompanying drawings, and the appended claims.

DRAWINGS

FIGS. 3A to 7D show the beneficial effect of a micellized full spectrum hemp oil over a period of 60 days on 150 human subjects having Type II diabetes in a double blind randomized human clinical trial.

FIGS. 8A to 9C show the beneficial effect of a micellized full spectrum hemp oil in COVID-19 patients. The data were obtained by assaying weekly blood samples obtained from patients who coincidentally tested positive for the SARS-CoV-2 virus. FIGS. 9A, 9B, and 9C show the effect on pro-inflammatory cytokines TNFα, IL-1, and IL-6. The full spectrum hemp oil preparations that are formulated according to this disclosure can be used to lower the risk of cytokine storm in patients having signs or symptoms of COVID-19.

FIGS. 10A to 10C are taken from a clinical trial designed to study the effect of a micellized full spectrum hemp oil on sleep.

DETAILED DESCRIPTION

This disclosure provides a technology for preparing a cannabinoid mixture with special therapeutic benefits. It is illustrated by but not limited to a range of compositions that are distributed under the name Purzorb®, a registered mark for plant and herb extracts used in creams, lotions and cosmetic products, and in nutritional and dietary supplements. Purzorb is a range of pharmaceutically compatible products produced by a process that micellizes a decarboxylated full spectrum hemp oil into a preparation that is suitable for oral ingestion Animal models with Purzorb® have demonstrated a rapid and almost complete absorption (85%) in the intestinal lining using Franz diffusion apparatus.

Figure 1A:
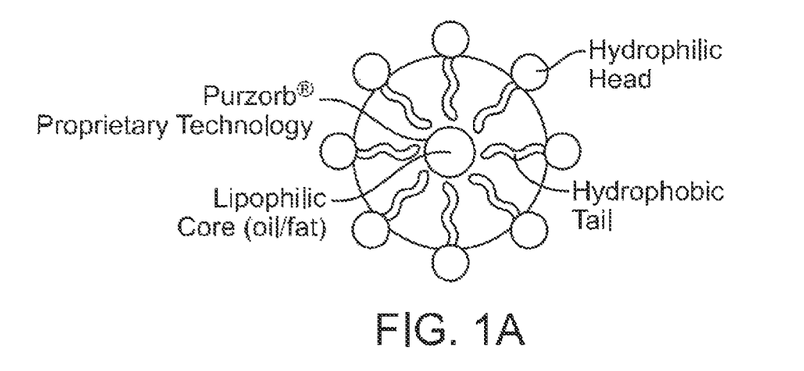
FIGS. 1A to 1C are concept images depicting micelle structure of a full-spectrum hemp oil CBD product (FIG. 1A), kinetics of pharmacotherapy (FIG. 1B), and extent of absorption (FIG. 1C).
Figure 1B:
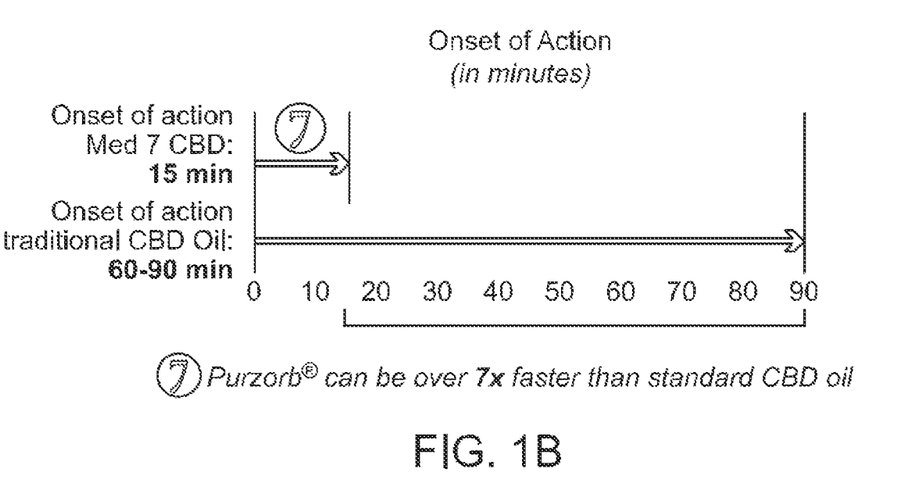
Figure 1C:
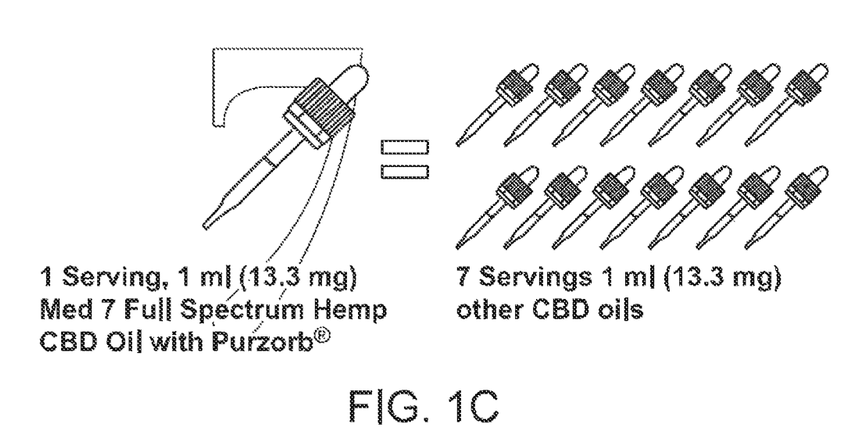

FIG. 1A depicts an exemplary full-spectrum hemp oil micelle, marketed under the mark Purzorb®. Each particle is approximately 22 nm in size, making it highly permeable in water. FIGS. 1B and 1C demonstrate that the onset of action and the potency of the composition in terms of cannabinoids delivered into the circulation is considerably higher than standard preparations of CBD oil.

The micellized preparations of full spectrum hemp oil provided in this disclosure represent a considerable advance over previous technology. The pharmacokinetic advantages include the following:
- Higher absorption: Micellized full spectrum hemp CBD oil has demonstrated 640% more bioavailability than unformulated hemp;
- More effective: just one drop of micellized full spectrum hemp CBD leads to a circulating level that is only achievable using 7 drops of competing CBD products;
- The reported onset of action of orally consuming micellized full spectrum hemp CBD oil can occur within 15 to 30 minutes;
- 85% absorption in the gastrointestinal tract: Micellized full spectrum hemp CBD oil has significantly more bioavailability than unformatted hemp oil. This means that the Med 7 can get the same effect quicker than that of a much higher dose of traditional CBD oil products.

Preparation of Full-Spectrum Hemp Oil

Cannabinoid oil used in the products described in this disclosure generally contain a full-spectrum industrial hemp oil. Such preparations contain not only CBD, but other cannabinoids described below that give the compositions many of their constitutional and therapeutic benefits.

Hemp oil can be obtained from varieties of *Cannabis sativa* that are bred to contain high levels of CBD, and low amounts of THC. In the U.S., hemp is classified in the Farm Bill by the federal government as cannabis containing no more than 0.3% THC by dry weight. Most of the cannabinoid-containing oil is recovered from the flower, resin on the stem, and the leaves of the hemp plant. The manufacturing process typically includes cleaning the agricultural product to over 99% before pressing the oil. Hemp extract can be purchased commercially, for example, from in Supply Labs, Northeast Hemp Commodities, and Bluebird Botanicals.

Extracting CBD from the hemp plant can be done, for example, by filtration. $CO_2$ extraction (supercritical or winterization) takes advantage of the differing solubility of waxes and cannabinoids at temperatures below the freezing point. Essentially, the frozen wax from the hemp plant containing CBD is stripped from the plant using carbon dioxide. The wax is then separated from the solvent using a filter press. Another method is a maceration process, known as Hemp Bio Mass. Ground-up hemp is mixed with a solvent such as ethanol, heptane or hexane. The solvent strips the CBD oil out of the plant fibers, and then the hemp oil/solvent combination is run through a filter press as a slurry. The solvent is then distilled off, resulting in pure hemp oil. The oil can then be further distilled and purified. Following extraction, the color of the product is generally dark brown or green due to the presence of chlorophyll. Activated carbon filtration using specialized carbon-infused filter media.

Filtration devices useful for preparation of hemp oil can be obtained, for example, from M.W. Watermark. If appropriate, different cannabinoids in the hemp oil can be separated from each other and/or discarded, for example, by high pressure liquid chromatography on columns such as the Alliance® HPLC 150 LC System, available from Waters Solutions.

As an alternative to purifying products from hemp oil, cannabinoid mixtures suitable for some of the uses provided in this disclosure can be prepared by combining purified or synthetic cannabinoids. Synthetic methods for CBD and related molecules are described, for example, by B. Jung et al., Chem Asian J. 2019 Nov 4;14(21):3749-3762, and A. Lago-Fernandez et al., Methods Enzymol. 2017;593:237-257.

The full spectrum hemp oil was prepared for the working examples in this disclosure as follows. The oil was extracted from a strain of *Cannabis sativa* (industrial hemp). Flowers and leaves of the hemp plant were collected and dried until the remaining moisture was approximately 10%. The plant material was ground to a size of 25 mesh, and extracted with supercritical CO2. The extract was dissolved into 70% ethanol, and cooled to −4 degrees C. to separate the waxes. The solution was filtered, and the de-waxed extract was passed through chromatographic columns to produce semi-purified oil. The solvents are removed from the oil, and batches are blended to produce the preparation subsequently used for micellization. This method is generally described in granted Chinese patents CN 107011125 B and CN 107381097 B.

By way of illustration, hemp oil preparations refined through super-critical $CO_2$ extraction and column chromatography contain approximately 81% cannabinoids shown in Table 1. Such preparations are available commercially under the trade name Hempco81 from Hempco Inc. (Lone Tree, Colorado). Subject to analysis, comparable preparations are available, for example, from Hempson Biotech and Kazmira LLC.

The proportionality of components of hemp oil before micellization is exemplified as follows. In terms of cannabinoid content, a typical analysis is shown in Table 1: The percentage of a compound in a solutions, solvent mixture, suspension, or proportion referred to in this disclosure is on a weight per weight basis, unless explicitly stated otherwise.

TABLE 1

Cannabinoid mixtures in full spectrum hemp oil preparations

| | Concentration | Proportion |
|---|---|---|
| Preparation A | | |
| THC (Δ9-tetrahydrocannabinol) | 0.13 mg/mL | 0.9% |
| THCV (tetrahydrocannabivarin) | 0.92 mg/mL | 6.1% |
| CBD (cannabidiol) | 11.90 mg/mL | 80.0% |
| CBDV (cannabidivarin) | 1.60 mg/mL | 10.7% |
| CBG (cannabigerol) | 0.32 mg/mL | 2.2% |
| Total | 14.87 mg/mL | 100.% |
| Preparation B | | |
| THC (Δ9-tetrahydrocannabinol) | 0.12 mg/mL | 0.8% |
| THCV (tetrahydrocannabivarin) | 0.41 mg/mL | 2.8% |
| CBD (cannabidiol) | 11.19 mg/mL | 76.5% |
| CBDV (cannabidivarin) | 2.44 mg/mL | 16.6% |
| CBG (cannabigerol) | 0.47 mg/mL | 3.2% |
| Total | 14.63 mg/mL | 100% |

The oil typically also contains a fatty acid composition is shown in Table 2:

TABLE 2

Fatty acid content of hemp oil preparations

| | Preparation A | Preparation B |
|---|---|---|
| Linoleic acid (18:2, omega-6) | 50.7% | 55.2% |
| Alpha linolenic acid (18:3 omega-3) | 17.1% | 20% |
| Gamma linolenic acid (18:3 omega-6) | 0.9% | 3.1% |
| Palmitic acid | 6.7% | 6.5% |
| Stearic acid | 2.5% | 2.5% |
| Oleic acid | 10.9% | 10.5% |
| Stearidonic acid | (not determined) | 1.2% |
| Eicosaenoic acid | 0.4% | 0.5% |
| Others | <1% | <1% |
| Vitamin E activity | 10.3 I.U. | 13-20 I.U. |

Micellization

To facilitate formulation and enhance bioavailability, the purified full spectrum hemp oil is optimally packed into micelles (a colloid suspended in an aqueous solvent). Micelles provide sustained and controlled release of macromolecules, provide chemical and physical stability of the encapsulated molecules, improve drug pharmacokinetics and favorable tissue distribution, and improve drug bioavailability.

The colloidal suspension is an emulsion of oil in aqueous solvent above the critical micelle concentration. A typical micelle in aqueous solution forms an aggregate with the hydrophilic portion of the molecule in contact with surrounding solvent, sequestering the hydrophobic single-tail regions in the micelle center. This phase is caused by the packing behavior of single-tail lipids in lipid layer. Difficulty filling all the volume of the interior, while accommodating the area per head group forced on the molecule by the hydration of the lipid head group, leads to the formation of the micelle.

FIG. 1A is a stylized depiction of a lipid micelle according to this invention. The core represents an aliquot of a cannabinoid oil preparation (full-spectrum hemp oil) to be delivered to and absorbed by the gastrointestinal tract of the subject being treated. The cannabinoid oil is wrapped in molecules having an outward facing hydrophilic head and an inward facing lipophilic tail. Such molecules may be characterized as amphipathic or amphiphilic, and function as a surfactant to allow the colloidal suspension to form. The amphipathic molecules in each micelle are tightly packed into a spheroid shape, represented by the outer circle.

In thermodynamic terms, the driving mechanism for micellization is an attraction between the surface and the surfactant head-group with low surfactant concentrations and the adsorption on hydrophilic surfaces. This means that the surfactant adsorbs at low surfactant concentrations with its head-group contacting the surface. The critical micelle concentration (CMC) is defined as the concentration of surfactants above which micelles form and all additional surfactants added to the system go to micelles. The Gibbs free energy can be approximated as:

$$\Delta G_{micellization} = RT \times ln(CMC)$$

where $\Delta G_{micellization}$ is the change in Gibbs free energy of micellization, R is the universal gas constant, T is the absolute temperature, and CMC is the critical micelle concentration. The self-assembly of amphiphilic molecules forms micelles. The structures contain hydrophilic/polar regions (head) and hydrophobic/nonpolar regions (tail). Micelles are formed in an aqueous solution whereby the polar region faces the outside surface of the micelle, and the nonpolar region forms the core.

To manufacture micelles, CBD containing oil or purified CBD is dissolved in a water miscible organic solvent. This solvent cannabinoid solution is mixed or injected into an appropriate aqueous environment. The dissolution of the organic solvent causes the dissolved cannabinoids to self-align into micro- or nano-micellar particles. Size, composition and concentration of the micelles are controlled by the chemical properties of the cannabinoids, the organic solvent/aqueous environment and the physical parameters of the solvent addition. In the alternative, micelles can be formed by sonication. See, for example, U.S. Pat. Nos. 8,808,734 and 10,258,601. Preparation and use of cannabinoid micelles and formulations is also put forth in U.S. Pat. Nos. 9,839,612, 10,456,357, and 10,568,865, and in US 2019/0183853 A1 and US 2020/0061138 A1. Exemplary amphipathic molecules suitable to constitute the outer shell of the micelle are any one of the following: polyethylene glycol (PEG) 40 hydrogenated castor oil, polyethylene glycol-phosphatidylethanolamine (PEG-PE), poly(N-vinyl pyrrolidone) (PVP), poly(N-isopropylacrylamide) (pNIPAM), poloxamer 407, poloxamer 188, poloxamer 85, and tocopherol methoxypolyethylene glycol succinate (TPGS); or a combination of two or more thereof.

Once formed, the micelles can be separated from solutes in the aqueous phase, and formulated for clinical use or commercial distribution. Micelles are preferably less than 500, 200, 100, 50, or 30 nm in size, preferably over 10 nm in size, preferably about 20 nm in size, or within the following ranges: 5 to 500, 5 to 200 nm, 10 to 100 nm, 10 to 50 nm, or 15 to 30 nm. A preparation of cannabinoids in a form that "consists essentially" of micelles of a certain size by definition has no more than 20% and preferably no more than 10% or 5% of the cannabinoids present as micelles of other sizes, in solution, or in forms not characterized as micelles.

Composition of the Product

Pharmaceutically compatible micelles that have beneficial properties illustrated in this disclosure may be obtained from full spectrum hemp oil as described above. They may be characterized as containing the ingredients shown in Table 3.

TABLE 3

Analysis of micelle composition

| | Weight % | Concentration | Proportion |
|---|---|---|---|
| THC (Δ9-tetrahydrocannabinol) | N.D. | N.D. | 0% |
| THCV (tetrahydrocannabivarin) | 0.02 | 0.18 mg/mL | 4.9% |
| CBD (cannabidiol) | 0.32 | 3.11 mg/mL | 84.3% |
| CBDV (cannabidivarin) | 0.02 | 0.21 mg/mL | 5.7% |
| CBG (cannabigerol) | 0.01 | 0.07 mg/mL | 1.9% |
| CBC (cannabichromene) | 0.01 | 0.12 mg/mL | 3.2% |
| Total | 0.38 | 3.69 mg/mL | 100% |

Not detected (N.D.) means less than 0.01 wt. %. Besides THC (Δ9-tetrahydrocannabinol), other cannabinoids tested but not detected were CBN (cannabinol), THCA (tetrahydrocannabinolic acid), CBDA (cannabidiolic acid), CBGA (cannabigerolic acid), D8-THC (Δ8-tetrahydrocannabinol), and exo-THC (exo-tetrahydrocannabinol). CBD micelle preparations may contain at least 0.20 and preferably at least 0.30 wt. % of CBD, at least about 0.01 wt. % of THCV, CBDV, optionally CBG, and optionally CBC, and less than 0.03 or less than 0.02 wt. % of THC.

The mixture of cannabinoids together is typically at least 0.1, 0.3, or 0.5 weight %, or a range of 0.1 to 1.0 weight percent. More concentrated solutions are possible, but will typically require dilution before oral consumption. Proportionally (in terms of the total cannabinoid content), a product claimed below that contains "full spectrum hemp oil" has a mixture of cannabinoids, including a CBD content of at least 60% and preferably at least 70% (wt/wt) or at least 80%, with a typical working range of 60 or 70% to 95%. Proportionally (in terms of the total cannabinoid content), the product typically also has the following components in any combination:

- a THCV content of at least 2 or 3%, with a typical working range of 1% to 10%;
- a CBDV content of at least 3, 5, or 10%, with a typical working range of 3 to 20%;
- a CBG content of at least 1 or 2%, with a typical working range of 1 to 5%;
- a THC content less than 1%.

A premise of this disclosure is that the minor cannabinoids, specifically the varins THCV and CBDV help achieve the clinical effects demonstrated below. The hemp oil used to make the micellized preparations used in the trials contained naturally occurring CBDV and THCV: specifically, CBDV (between 4%-18%) and THCV (between 1% and 15%). Unless explicitly stated otherwise, the term full spectrum hemp oil is an oil that includes CBD, CBDV, and THCV in the ranges stated above. Micellized preparations of full spectrum hemp oil are sometimes referred to in this disclosure as "CBD oil" or "Med 7" as shorthand. These preparations also contain CBDV and THCV.

In jurisdictions where THC is subject to regulatory constraints, the THC concentration of the final preparation will be in compliance with said requirements: i.e., below 1%, and not more than 0.3% on a dry weight basis in the U.S. In jurisdictions and contexts where the manufacture and sale of THC is permitted for medical or recreational use, the micellized preparations of hemp oil may contain a relative THC content of 1 to 5%; or above 2%.

Unless otherwise constrained, full-spectrum hemp oil may be purified as a mixture from hemp plant, or alternatively made by combining isolated or synthetic cannabinoids to the concentrations specified.

Formulation with Other Ingredients

Therapeutically beneficial compositions according to this disclosure optionally include additional agents that operate independently or synergistically with cannabinoids present in the micelles. Compositions also optionally include non-medicinal components, such as a flavoring to enhance palatability, preservatives to improve shelf life, solvents or fillers to adjust concentration and enhance dispensation, and other pharmaceutically compatible excipients.

An additive of particular interest is cinnamon and extracts thereof Cinnamaldehyde is the main component of *Cinnamomum zeylanicum* or *Cinnamomum cassia* extracts. It has been described as being an antithrombotic (J. Huang et al., Thromb Res. 2007;119(3):337-342), an anti-inflammatory (U. Huss et al., J Nat Prod. 2002;65(11):1517-1521), and an anti-cancer agent (H.K. Kuan et al., Cancer Lett. 2009;278 (2):174-182). Cinnamaldehyde-containing micelles can be prepared, which induce relaxation of coronary arteries so as to be useful both to relieve coronary vasospasm and for therapeutic drug delivery (G. Raffai et al., Int J Nanomedicine. 2014; 9: 2557-2566).

As an alternative or in addition, another component of potential interest is clove, and extracts thereof. Oil from clove (*Syzygium Aromaticum*) typically contains at least 80% eugenol and is also reported as having anti-microbial, anti-fungal, and anti-inflammatory activities (A B Wicaksonon et al., IOP Conf. Series: Journal of Physics: Conf. Series 1295 (2019)012072.). Micelle preparations of clove is described by A.B. Wicaksonon et al., supra, and O. Thonggoom et al., J Microencapsul. 2016 May; 33(3):239-48.

Other essential oils may also be included in the formulation. An "essential oil" is a concentrated hydrophobic liquid containing volatile chemical compounds from a plant from which it is extracted. Cinnamon, clove, and other essential oils are generally extracted by distillation, often by using steam. Other processes include expression, solvent extraction, sfumatura, absolute oil extraction, resin tapping, wax embedding, and cold pressing. Optionally, the oils can be combined with the hemp oil, forming a combined core in a micelle manufacturing procedure. More typically, hemp oil and flavor oils are micellized separately, and then mixed to make the final formulation. This allows the manufacturer to produce several products or variations from a standard supply of micellized hemp oil.

Depending on the intended purpose and market of a product, additional additives of interest include sweeteners and preservatives. For purposes of improving sleep quality, possible additives include herbal mixtures or extracts that reduce sleep latency, such as valerian and/or skullcap. For purposes of improving alertness, elevating mood, or overcoming a hangover, the preparation may contain a therapeutically effective amount of caffeine.

By way of illustration, formulation with cinnamon, cloves, sweeteners, preservatives, and carriers, a typical product for commercial distribution may contain the ingredients shown in Table 4.

TABLE 4

Ingredients of Med 7 product

| | | % | g per bottle |
|---|---|---|---|
| 1 | water | 53.6 | 31.7 |
| 2 | sodium benzoate (preservative) | 0.07 | 0.04 |
| 3 | monk fruit | 0.12 | 0.07 |
| 4 | sucralose (sweetener) | 0.68 | 0.40 |
| 5 | xylitol (sweetener) | 0.75 | 0.44 |
| 6 | stevia (sweetener) | 0.75 | 0.44 |
| 7 | natural flavors | 1 | |
| 8 | masking liquid | 7.0 | 1.9 |
| 9 | PurZorb Cinnamon flavor | 1.7 | 1.01 |
| 10 | PurZorb Clove flavor | 1.4 | 0.84 |
| 11 | Hempzorb81 ™ (full spectrum hemp oil formulated with Purzorb technology) | 28.5 | 16.8 |
| 12 | citric acid (adjust pH to 3.7-4.0) | 0.17 | 0.10 |
| | Total | 100 | 77.8 |

In terms of the preparation as a whole, current working ranges for commercial products include the components in the following proportions in any combination:

- Full-spectrum hemp oil in micelle form: at least 0.05% weight percent with a typical working range of 0.1 to 1.0%
- Cinnamon extract in micelle form: at least 0.5, 1, or 1.5%, with a typical working range of 1 to 4%;
- Clove oil extract in micelle form (if included): at least 0.5, 1, or 1.5%, with a typical working range of 1 to 4%.

Pharmacology and Packaging

In pharmaceutical use, cannabinoids are pleotropic. CBD has low affinity for the cannabinoid CB1 and CB2 receptors, but can act as an antagonist of CB1/CB2 agonists. CBD may also be an antagonist of GPR55, a G protein-coupled receptor and putative cannabinoid receptor that is expressed in the caudate nucleus and putamen in the brain. It also may act as an inverse agonist of GPR3, GPR6, and GPR12 CBD has been shown to act as a serotonin 5-HT1A receptor partial agonist. It is an allosteric modulator of the μ- and δ-opioid receptors as well. The pharmacological effects of CBD may involve PPARλ agonism and intracellular calcium release.

Full spectrum hemp oil has potential as mood stabilizers (anti-anxiety agents), analgesic agents for arthritis, osteoarthritis, and joint sprain (decreasing joint pain), anti-inflammatory agents (measurable by circulating levels of C-reactive protein, TNF-α, IL-6, and erythrocyte sedimentation rate), lipid health (measurable by HDL, LDL, and homocysteine levels), and diabetes (such as Type II diabetes, measurable by circulating glycated hemoglobin HbA1c levels).

A composition is referred to in this disclosure as effective in the treatment of a particular condition if the compositional makeup, the amount of each active component, and the formulation of the composition can demonstrably improve symptoms or signs of the condition in at least some humans or other subjects administered with the composition, compared with a control population, whether or not the composition is actually used for such purpose. By way of illustration, improvement may include improving one or more serum markers or clinical features that are characteristic of the condition, decreasing pain or other symptomatology, or otherwise improving the quality of life for the treated subject. For Type II diabetes, the treatment is effective if there is an improvement in circulating HbA1 c levels, resting glucose levels, improved glucose tolerance, improved dietary management or dietary flexibility, or an improvement or delay of any adverse consequence of Type II diabetes, such as neuropathy, retinopathy, nephropathy, hearing loss, dermopathy, and sleep apnea, in any combination.

For distribution as commercial products, the preparations put forth in this disclosure are optionally packaged as a kit with or otherwise accompanied by information describing the use of the preparations in the treatment or clinical management of any of these conditions, either alone or in combination with other therapeutic agents. The promotion of a commercial product in any forum and in any format so as to invoke or imply treatment or management of particular clinical condition with or without a prescription that is in accordance with patent claims issuing from this disclosure without having a license to do so constitutes an inducement to infringe said claims.

Pharmacokinetics

Figure 2A:
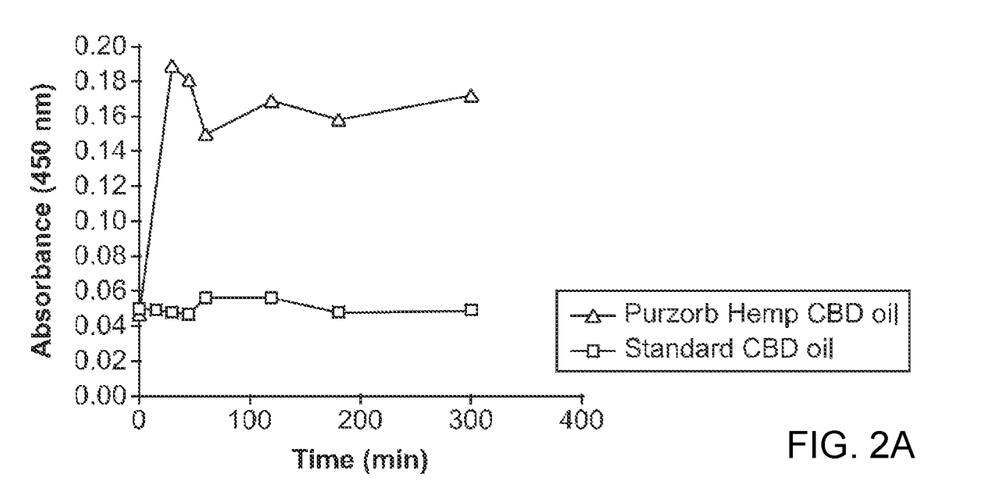
FIG. 2A compares absorption of Purzorb® full spectrum hemp oil compared with standard CBD oil (formulated in medium chain triglycerides, MCT) in an animal intestinal model.

FIG. 2A shows pharmacokinetics of high spectrum hemp oil measured in an animal model. The study demonstrated a rapid and almost complete absorption in the intestinal lining using Franz diffusion apparatus. (PHRX, 2016).

A subsequent small-scale clinical trial was run to evaluate the blood levels of Purzorb® orally administered to human subjects over a 12 hour period.

Seven subjects participated for a period of twelve hours. At the onset, each subject had arterial blood drawn to set the baseline of CBD in their circulation. Each had a baseline of 0.0 mg of CBD. Each subject was given an oral dose of one vial with 8.95 mg of CBD. Vials were prepared by PurhealthRX, and delivered to the study investigator. Each subject was given a vial, and instructed to spray the liquid under their tongue and hold it there for 30 seconds before swallowing. The nurse in attendance let each subject know when their 30 seconds was up so they could swallow the remaining liquid. Blood was drawn periodically, and CBD levels were measured by high pressure liquid chromatography (HPLC).

Figure 2B:
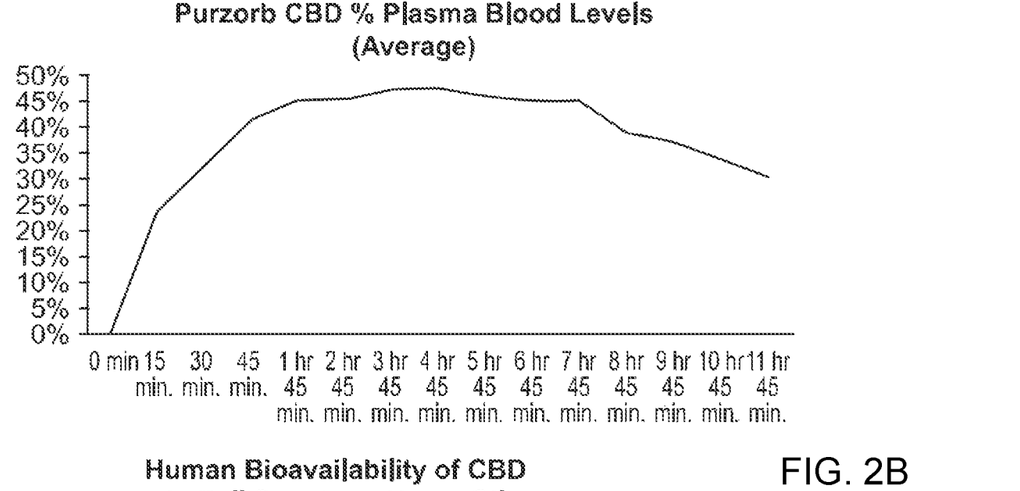
FIG. 2B shows average plasma blood levels of CBD measured in seven human subjects prior to adjustment for blood volume.
Figure 2C:
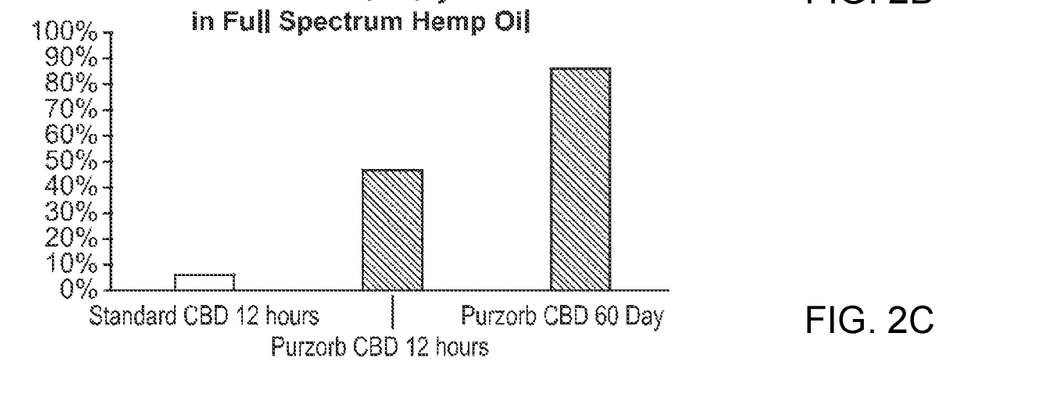
FIG. 2C shows the accumulation of CBD when administered daily for about two months.

FIG. 2B shows the results. The onset of Purzorb® in blood is rapid, and has a lasting duration. Patients had over 50% of the available CBD in their blood stream by the first measurement of 15 minutes. This exceeds what has been shown with CBD or THC that has been inhaled or vaped. The blood levels measured significantly higher than what has been seen with standard CBD oil and other solubilizing methods. FIG. 2C shows that the bioavailability of Purzorb exceeds 80% after 60 days of daily dosing.

Therapeutic Effects Measured in a Human Clinical Trial

Safety and potential therapeutic effects of Purzorb® Full Spectrum Hemp Oil (available under the trade name Med 7™). The serving size was 2 mL of the Med 7 cinnamon flavor. The amount of CBD in each 2 mL serving was 10 mg. Placebo product was 1.0 mg per 2 mL. Subjects were instructed to take a 2 mL dose once daily. No other change to diet, fluid intake, or exercise was recommended.

This was a double-blind, placebo-controlled, multisite, and randomized effectiveness study performed on human subjects. Mean Age=55±5 years old; Male:Female ratio=58:2. Initial screening of subjects completed before the baseline data was taken for this test included: AST, ALT, to assess liver function, creatinine and BUN, TSH for the evaluation of the thyroid and to help evaluate kidney function, a standard RBC, CBC, and platelets were drawn and evaluated for Wellness. Each of these tests was run on arterial blood drawn following standardized protocol for the procedures and completed by healthcare professionals.

Inclusion criteria: Subjects who signed a written informed consent consistent with required guidelines and met prior to participation in the trial, were 18 years of age or older, not on any medication or dietary supplement, have normal kidney, liver, and thyroid functions, and normal CBC prior to the start date of this study, and able to follow the protocol as designed.

Exclusion criteria were as follows: History of head trauma; history of serious diseases or illness diagnosed at this time; known moderate to severe renal insufficiency; recent history (<6 months prior to Visit 1) of myocardial infarction; subjects who regularly use oxygen therapy; subjects with known active tuberculosis; subjects with a history of cancer within the last 5 years; subjects who have undergone thoracotomy with pulmonary resection within 1 year prior to the trial; subjects who are currently in a pulmonary rehabilitation program or who have completed a pulmonary rehabilitation program in the 6 weeks prior to the screening visit (Visit 1); subjects currently prescribed diuretic medications, cardiac stimulants, or any other prescribed or non-prescribed medication that may, in the opinion of the Clinical Studies USA staff, alter testing results; use of opiate analgesics prescribed or otherwise obtained for any treatment reason including migraine treatment or for recreational purposes; history of drug or alcohol addiction; females who are pregnant, lactating, or nursing or who may become pregnant during the course of the study; patients diagnosed as HIV-positive, diagnosed with AIDS, or with any neuromuscular condition including cerebral palsy (CP), multiple sclerosis (MS), amyotrophic lateral sclerosis (ALS), or Huntington's Chorea; patients with uncontrolled hypertension (e.g. blood pressure>150/100); subjects who have used steroid therapy within the last 6 months; or subjects with any condition not previously named that, in the opinion of the investigators or intake staff, would jeopardize the safety of the patient or affect the validity of the data collected in this study.

Anxiety

Figure 3A:
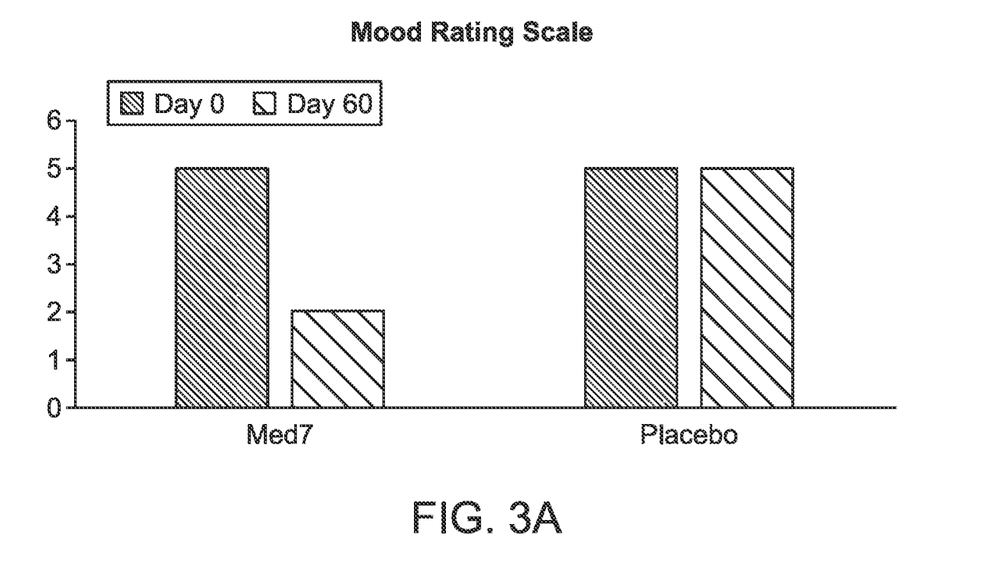
FIG. 3A shows measures of anxiety on a mood rating scale.

Anxiety was evaluated using an online testing system of evaluation questions. Patients used computers to report their baseline and results. A predefined subjective Mood Rating Scale was used to assess anxiety and current mood. The MRS was as follows:
1—Happy
2—Mostly Happy
3—Intermittently Happy
4—Sometimes Happy
5—Some Anxiety
6—Mild Anxiety
7—Some Periods of High Anxiety
8—Half the Time Anxiety is Dominate
9—Manageable Anxiety
10—Mostly Feeling Anxiety FIG. 3A shows the results. In the Med 7 study product group, Day 0 average was (5) some anxiety; Day 60 average was (2) mostly happy. 91% of the subjects in the Med 7 product group reported longer sleep with more periods of dreaming. Results in the placebo product group were as follows: Day 0 average was (5) some anxiety; Day 60 average was (5) some anxiety; no changes in sleep were reported. Purzorb CBD has shown a trend toward a reduction of anxiety, and also promoted sleep.

Joint Pain

Most commonly, joint pain is attributable to arthritis or arthralgia, which is inflammation or pain from within the joint itself Joint pain can be mild, causing soreness only after certain activities, or it can be severe, making even limited movement, particularly bearing weight, extremely painful. We did not try to identify a disorder for the joint pain in this study.

Joints that were reported as being sore or in pain by fifty-six of the subjects in this study. The joints of these patients were evaluated for pain by measuring of the joint, evaluation of localized heat, evaluation of swelling, and range of motion. Initial evaluation was completed on Day 0, and final evaluation was completed on Day 60. Fifty-one subjects reporting joint pain were in the live product group. Subjects on average reported a drop in pain levels of at least two levels.

Pain levels were assessed according to the following subjective scale:
1—No pain;
2—Mild pain—completely normal movement, no limits;
3—Moderate pain—20% decrease in normal movement, some limits of daily use;
4—Intermittent severe pain—up to 50% decrease in normal movement, some limits of daily use;
5—Severe pain—up to 80% decrease in normal movement, more limits of daily use;
6—Constant severe pain—up to 100% pain in normal movement or no movement.

On Day 0 of this study, 36 subjects in the live product group on Day 0 were #3, 7 subjects in the live product group on Day 0 were #2, and 8 subjects in the placebo group on Day 0 were #3. On the final Day 60 of this study, 31 subjects in the live product group were at level #2, 12 subjects in the live product group were at level #1, and 8 subjects in the placebo group were at #3.

Thus, the micellized hemp oil preparation was effective in moving a majority of patients from the #3 category to #1 or #2, whereas the placebo had no effect. The beneficial effects are believed to be mediated via anti-inflammatory effects of the combination of cannabinoids in the micellized full-spectrum hemp oil.

C-Reactive Protein

C-reactive protein (CRP) levels increase when there is inflammation in the body. The testing method in this study was with an immunochemiluminometric assay, and interpreted as follows:
CRP level of lower than 1.0 mg/L—low risk of heart disease;
CRP level of 1.0 mg/L and 3.0 mg/L—moderate risk of cardiovascular disease (CVD);
CRP level of more than 3.0 mg/L—high risk of CVD.

Figure 3B:
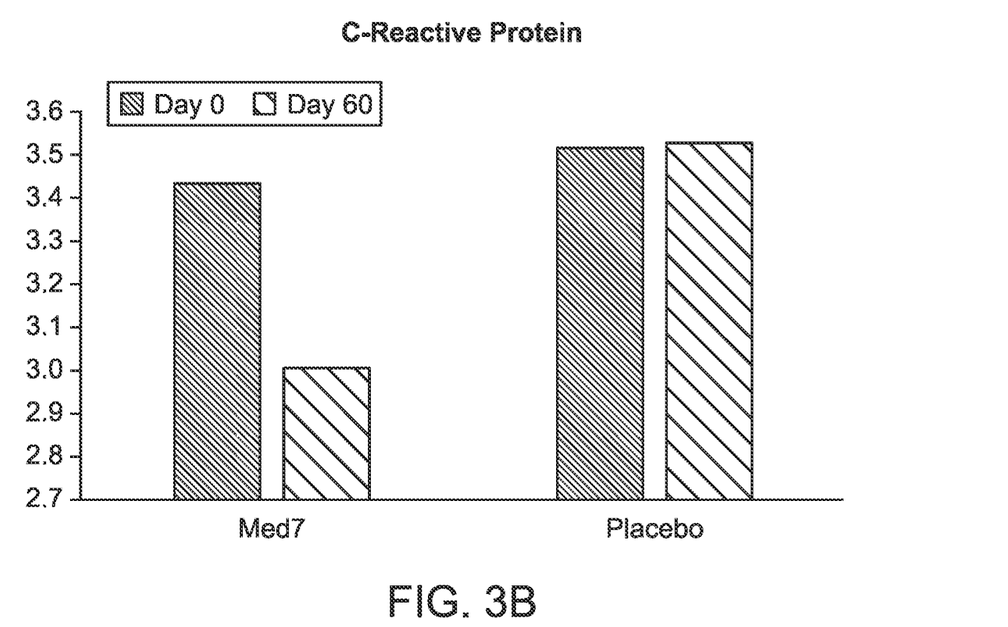
FIG. 3B shows the circulating level of C-Reactive Protein (CRP, mg/L) measured in the Med 7 treated group and placebo group.

FIG. 3B shows the results. For the Med 7 study product group, the Day 0 average was 3.436; and the Day 60 average was 3.012. For the placebo product group; Day 0 average was 3.52; and day 60 average was 3.53

Tumor Necrosis Factor

Tumor necrosis factor (TNFα) is a multifunctional pro-inflammatory cytokine that plays important roles in diverse cellular events such as cell survival, proliferation, differentiation, and death. In some circumstances, it also promotes cancer. The testing used was an enzyme-linked immunosorbent assay (ELISA).

Figure 4A:
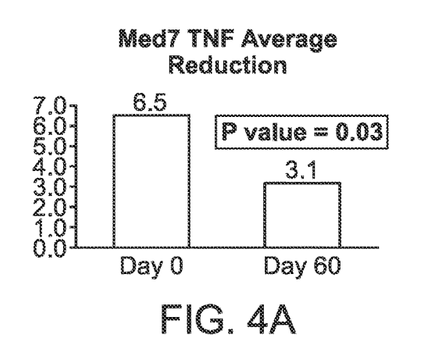
FIG. 4A shows the circulating level of Tumor Necrosis Factor (TNFα, ng/L).

FIG. 4A shows the results. Normal TNF levels are 0 to 5 ng/mL. For the Med 7 study product group, the Day 0 average was 6.52 ng/mL, Day 60 average was 3.14 ng/mL. For the placebo product group, Day 0 average was 2.6 ng/mL; Day 60 average was 2.3 ng/mL.

Interleukin 6

Interleukin 6 (IL-6) is a multifunctional cytokine. IL-6 is thought to have a central role in host defense mechanisms. Deregulation of IL-6 gene expression is involved in the pathogenesis of polyclonal and monoclonal B cell abnormalities, such as rheumatoid arthritis and multiple myeloma. IL-6 levels were measured by ELISA.

Figure 4B:
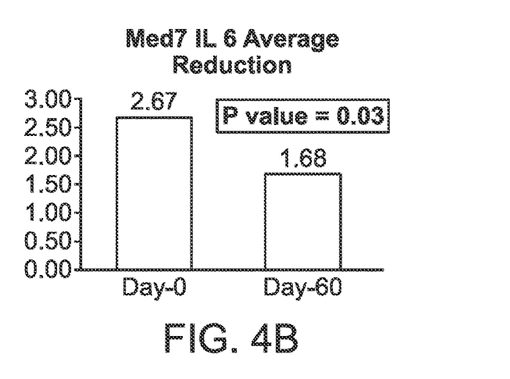
FIG. 4B shows a reduction in the circulating level of interleukin 6 (IL-6, ng/L).

FIG. 4B shows the results. Normal levels are 1.8 pg/mL. In the Med 7 study product group, Day 0 average was 2.67 pg/mL; Day 60 average was 1.68 pg/mL. In the placebo product group, Day 0 average was 3.47; and Day 60 average was 3.29 pg/mL.

Erythrocyte Sedimentation Rate

An elevated EST can identify and measure general inflammation in the body. EST test results that are higher than normal are associated with inflammation, including autoimmune diseases, such as lupus, certain types of arthritis, including rheumatoid arthritis, Waldenstrom's macroglobulinemia (a rare cancer), temporal arteritis, polymyalgia rheumatica (causing muscle and joint pain), hyperfibrinogenemia, and allergic or necrotizing vasculitis. Some types of infection that cause high EST are bone infection, heart infections causing myocarditis, pericarditis, endocarditis, rheumatic fever, skin infection, systemic infections, and tuberculosis (TB).

EST was measured as the amount of plasma remaining at the top of the test tube after 1 hour. Normal values are 0 to 20 mm/hr.

Figure 5:
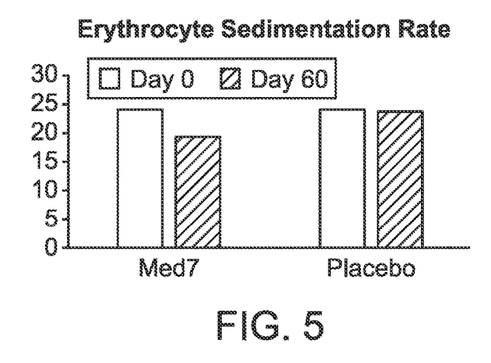
FIG. 5 shows the erythrocyte sedimentation rate (EST, mm/h).

FIG. 5 shows the results. In the Med 7 study product group, Day 0 average was 24.2; Day 60 average was 19.52. In the placebo product group, Day 0 average—24.16; Day 60 average—23.88. The final data average for this group moved into the Wellness area. Eighty-two of the subjects in this group had their data move into the Wellness area. Eighteen subjects of this group had numbers slightly above twenty, but they have had a significant move into a better Wellness area.

High Density Lipoprotein

HDL cholesterol may act in a variety of beneficial ways that tend to reduce the risk for heart disease. HDL cholesterol scavenges and removes and recycles LDL from plaques, transporting it to the liver where it is reprocessed. HDL levels greater than 60 mg/dL are considered to be beneficial. HDL cholesterol levels less than 40 mg/dL are considered to be adverse.

Figure 6A:
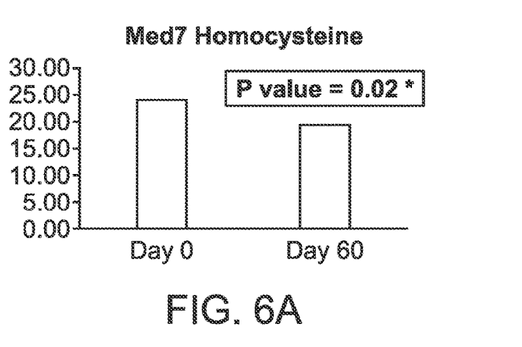
FIG. 6A shows the circulating level of homocysteine (μmol/L).
Figure 6B:
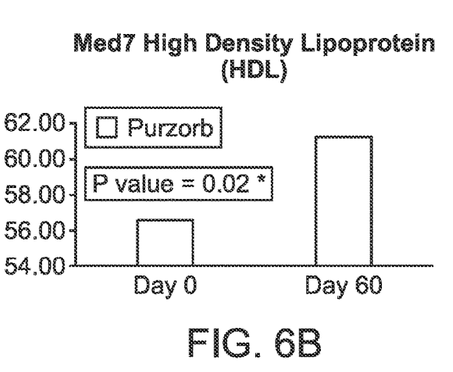
FIG. 6B shows the circulating level of High Density Lipoprotein (HDL, mg/dL).
Figure 6C:
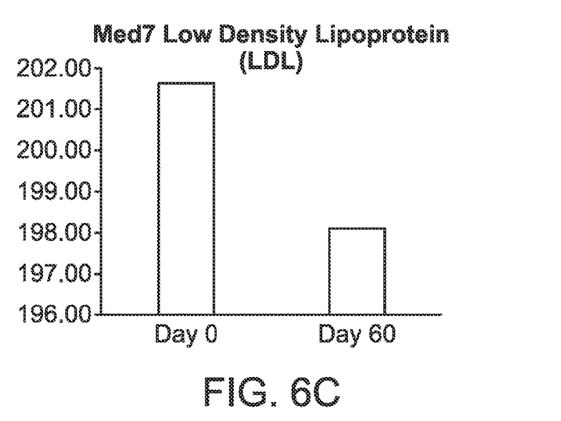
FIG. 6C shows the circulating level of Low Density Lipoprotein (LDL, mg/dL).

FIG. 6B shows the results. In the Med 7 study product group, Day 0 average was 56.62; Day 60 average was 61.27. In the placebo product group, Day 0 average was 50.1; Day 60 average was 49.9. The one hundred subjects in the Med 7 Product Group showed a significant change in their HDL numbers into more Wellness numbers Low Density Lipoprotein LDL can indicate higher cholesterol concentrations in plaques, causing atherosclerosis, leading to coronary artery disease, and increasing the risk of heart attacks and strokes. Normal levels are 150 to 199 mg/dL FIG. 6C shows the results In the Med 7 study product group, Day 0 average was 201.6 mg/dL; Day 60 average was 198.1 mg/dL. In the placebo product group, Day 0 average was 191.86 mg/dL; and Day 60 average was 191.0 mg/dL.

Homocysteine

Having elevated levels of homocysteine in the blood (hyperhomocysteinemia) is associated with atherosclerosis, blood clots, heart attack, stroke, clot formation, the risk of deep vein thrombosis (DVT) and possibly the development of Alzheimer's disease. An elevated homocysteine level in the body does not in itself cause any symptoms.

The testing method used was automated fluorescence polarization immunoassay. Normal homocysteine levels are 4 to 15 µmol/L.

FIG. 6A shows the results. In the Med 7 study product group, Day 0 average was 24.2 µmol/L; Day 60—average was 19.52 µmol/L. In the placebo product group, Day 0 average was 19.42 µmol/L; Day 60 average was 19.86 µmol/L. A significant decrease in homocysteine was measured in the Med 7 group into a more Wellness set of numbers.

HbA1c

The A1c test measures what percentage of hemoglobin is coated with sugar (glycated). It reflects the average blood sugar level for the past two to three months. Normal A1c level is below 5.7 percent. Levels between 5.7 and 6.4 percent are considered prediabetes, indicating a high risk of developing diabetes in the future. An A1c level of 6.5 percent or higher on two separate is an indicator of active diabetes. An A1c level above 8 percent indicates diabetes is not well-controlled, with a higher risk of developing the complications. The testing method was the commercially available TS Diagnostics assay A1cNow®.

Figure 7A:
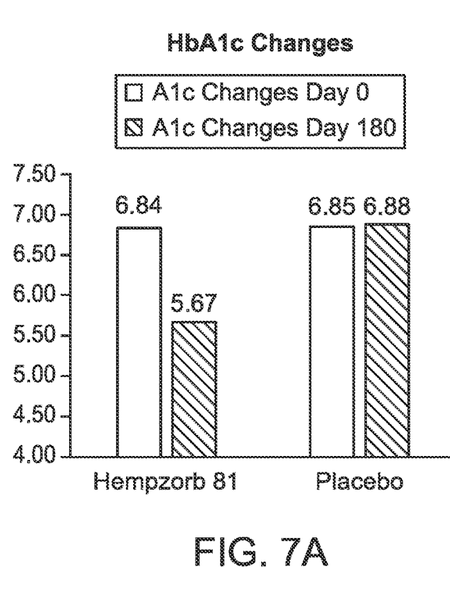
FIG. 7A shows an unexpected reduction in the circulating level of percent glycosylated hemoglobin (HbA1c) in patients having Type II diabetes.

FIG. 7A shows the results. In the Med 7 study product group, Day 0 average was 6.0 mmol/L; Day 60 average was 5.075 mmol/L. A significant decrease in A1c (about 20%) was measured in the Med 7 group into a more Wellness set of numbers.

Figure 7B:
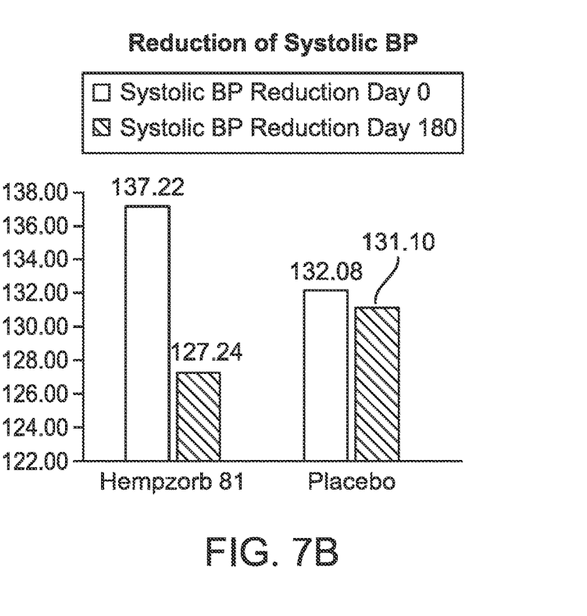
FIG. 7B shows a reduction in systolic blood pressure in the same patients.
Figure 7C:
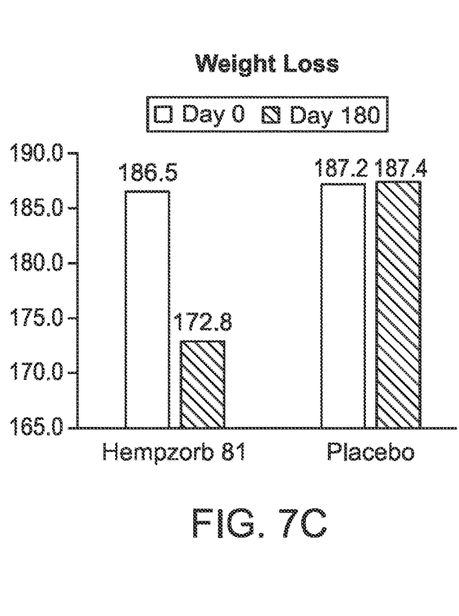
FIGS. 7C and 7D show weight loss (pounds) and girth reduction (inches).
Figure 7D:
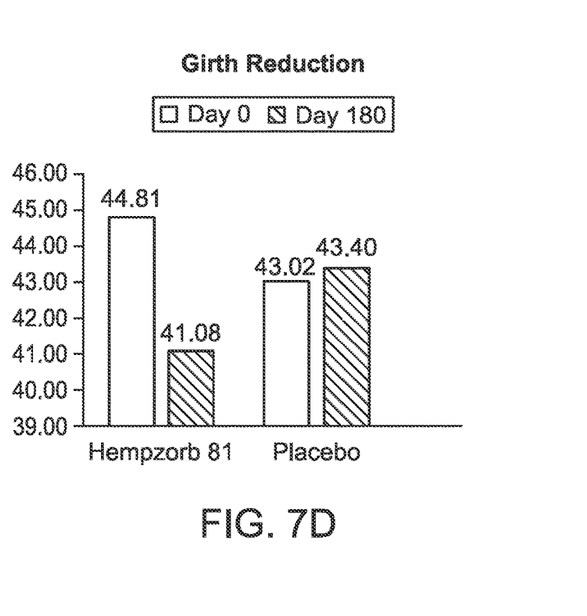

FIG. 7B shows a corresponding decrease in the systolic blood pressure in Med 7 treated patients of about 10 psi., moving them out of the range for Stage 1 hypertension. FIG. 7C shows a corresponding weight loss in the treated patients of about 14 pounds, moving their BMI out of the range for obesity. FIG. 7D shows a corresponding reduction in girth (almost 1 inch). All of these changes were significant at the $p<0.02$ level.

Conclusions

Therapeutic preparation of Purzorb® Full Spectrum Hemp Oil (Med 7) was shown in this study to be a safe way to use CBD. No side effects attributable to the hemp oil preparation were reported. No interactions were noted for the period of this study. Nine significant areas of Wellness showed a marked improvement. No statistically significant changes were measured in the control group for any of the tested areas. No subjects reported any reactions of interactions for the duration of this study.

The study patients on Med 7 reported positive effects on anxiety, joint pain and sleep. Inflammatory markers including TNF and IL-6 showed statistically significant reductions further demonstrating a propensity of the Med 7 to have a positive effect on key inflammatory markers. Other cardiovascular markers such as HDL and LDL also showed positive effects in the Med 7 study group.

Surprising and significant results were the beneficial lowering of circulating levels of HbA1c and homocysteine, which were both decreased in the Med 7 study group. There was a corresponding reduction in blood pressure and mass, to the patents' benefit.

Effects in COVID Patients

Purified cannabidiol (CBD) inhibits replication of SARS-CoV-2, the virus that causes COVID-19, and appears to promote the innate immune response of the host (L.C. Nguyen et al., bioRxiv, March 2021). However, one of the challenges to using CBD for treatment of COVID-19 patients is the lack of data showing that CBD positively affects the inflammatory sequelae on the host (B. Malinowska et al., Int. J. Mol. Sci. 22:1986, 2021). The makers of this invention have determined that micellized full-spectrum hemp oil is effective in decreasing the circulating levels of pro-inflammatory cytokines TNFα and IL-6, consequently also lowering the circulating level of C-reactive protein, an indicator of inflammation under way.

Since the study described in the previous section was done early in 2020, some of the 150 subjects entered into the study subsequently tested positive for SARS-CoV-2, the virus that causes COVID-19. This provided an unplanned and unexpected opportunity to determine whether the Med 7 cannabinoid preparations would have a beneficial effect in these subjects. For purposes of a control or placebo group, samples and data were obtained from the control arm of a separate study testing the efficacy of a SARS-CoV-2 vaccine Immunoassays were performed on blood samples taken from either population at about the time of diagnosis, and several weeks thereafter.

Figure 8A:
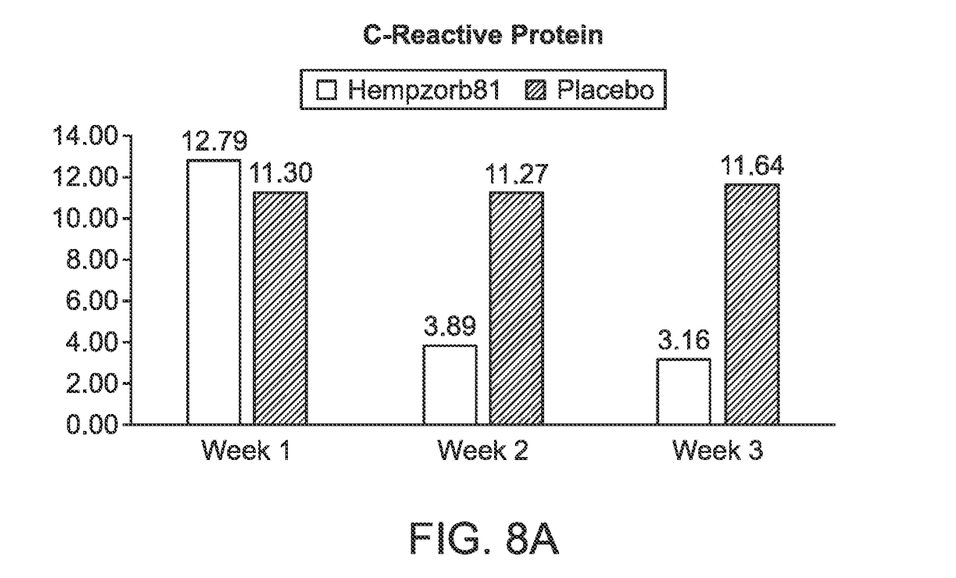
FIGS. 8A and 8B show respectively shows the effect on C-reactive protein (CRP) and white blood cell count (WBC), both markers for ongoing inflammation.
Figure 8B:
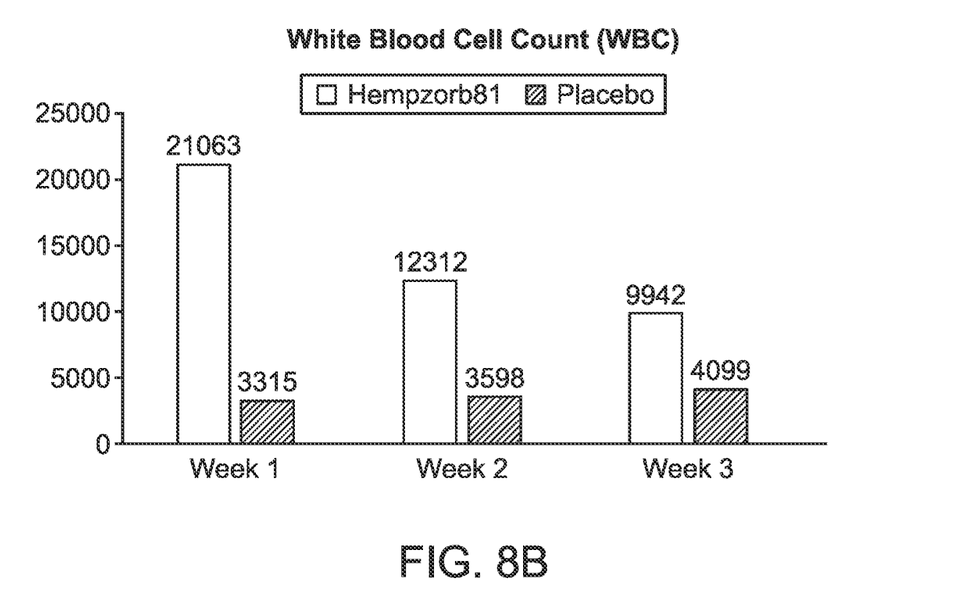
Figure 9A:
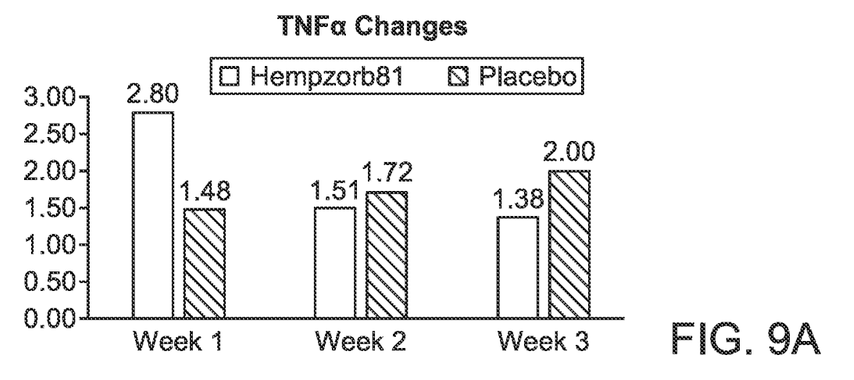
Figure 9B:
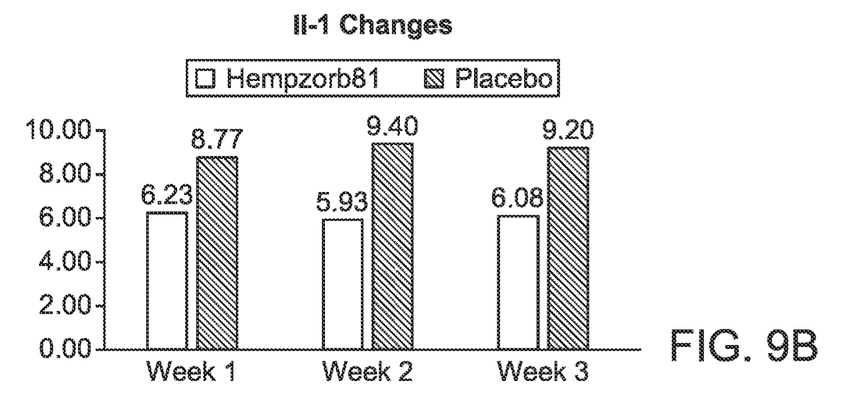
Figure 9C:
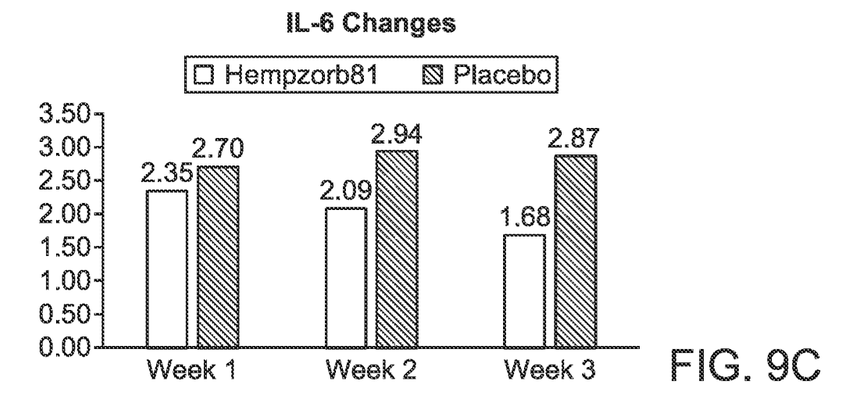

FIGS. 8A and 8B shows that the subjects treated with Med 7 had about a 3-fold decrease in circulating levels of C-reactive protein (CRP) and white blood cell count (WBC), both markers of ongoing inflammation. FIGS. 9A, 9B, and 9C show the levels of TNFα, IL-1, and IL-6 in the subjects consuming Med 7 and the controls. Consumption of Med 7 caused a significant and substantial decrease over time in the level of TNFα and IL-6.

This is important, because the ancillary organ failure that accompanies a severe case of COVID-19 is thought to be at least in part the result of a cytokine storm a production of pro-inflammatory cytokines that induces an extent of inflammation that has adverse consequences for the host. Oral administration of the micellar cannabinoid preparations described here can be valuable part of a clinical therapy to lessen the severity and consequences of the infection resulting from a cytokine storm.

These data are by way of illustration of a broader applicabililty. The data shows that consumption of Med 7 reduces the circulating levels of pro-inflammatory cytokines, resulting in a dampening of the sequelae of inflammation in two circumstances: joint pain, and infection with SARS-CoV-2. By analogy, other infections that induce cytokine storm should be amenable to treatment in the same way: for example, infection with other corona viruses, and other viruses and infectious agents with an inflammatory related pathology, such as influenza.

Benefits of Micellized Full Spectrum Hemp Oil for Sleep Quality

Some subjects from these earlier studies volunteered to participate in a follow-on study to determine whether Med 7 has an effect on sleep patterns. They were withdrawn from treatment with Med 7 for two weeks, to provide a wash-out period. They were equipped with a wearable device that monitors movement: specifically, the Charge 3 model distributed by Fitbit Corporation. The device has accelerometers to detect movement of the wearer in three dimensions, and also measures heart rate. It has an algorithm that determines from the input data the time the wearer is ready to sleep (the sleep period), calories consumed per day, and what proportion of the time is spent lying awake, and in the three stages of sleep: light sleep, deep sleep, and REM sleep.

There were two treatment groups of 50 subjects, and a negative control group of 50 subjects. The treatment groups were provided with a sufficient amount of Med 7 on a daily basis for 180 days. All groups were contacted by phone twice a week.

Figure 10A:
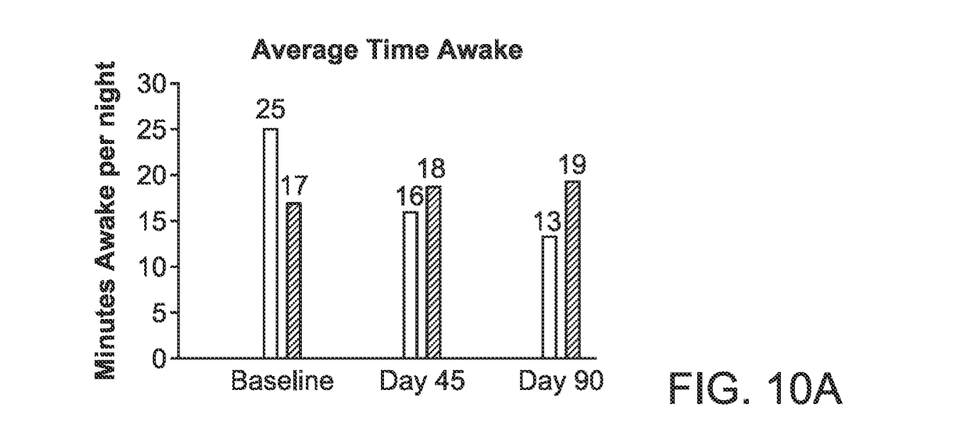
FIG. 10A shows sleep latency.
Figure 10B:
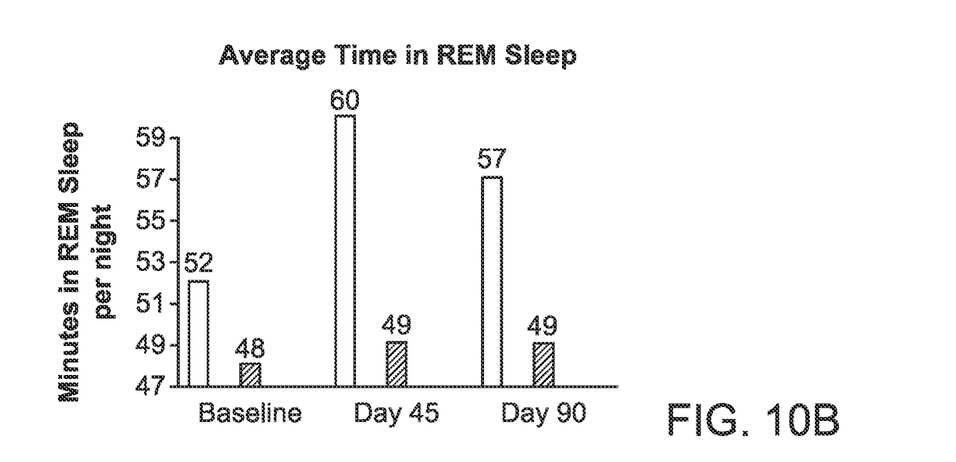
FIG. 10B shows the mean time per night spent in REM sleep.
Figure 10C:
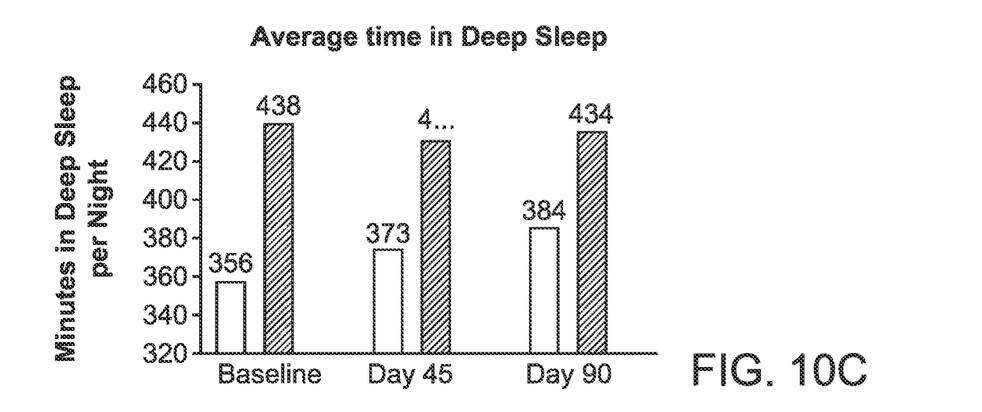
FIG. 10C shows the mean time per night spent in deep sleep. Remarkably, the mean time spent in deep sleep increased by about one hour.

FIGS. 10A, 10B, and 10C show the data combined for the two treatment groups on a nightly basis for sleep latency, REM sleep, and deep sleep.

Group 1 received a Med 7 dose of 4 mL per day (225 mg of Hempzorb81). There was a decrease in 90 calories burned in 24 hours by day 90. Deep sleep was increased on average by 50 minutes. REM sleep increased by 90 minutes. Sleep latency decreased by an average by about half. Group 2 received a Med 7 dose of 3 mL per day (170 mg of Hempzorb81). They had a decrease of 59 calories per day by Day 90. Deep sleep was increased by 5 minutes, and REM sleep increased by 1 minute. Sleep latency decreased by an average of 8 minutes per night. The control group had little to no change in calories burned per day. Awake time increased by an average of 2 minutes, REM sleep time didn't change, and deep sleep actually decreased by an average of 4 minutes.

The data show that micellized full-spectrum hemp oil preparations according to this invention improve sleep quality in several ways: reducing sleep latency, and improving the sleep time that is spent in deep sleep or REM sleep. By analogy with the cytokine and inflammation data, Med 7 treated COVID-19 patients will also benefit in terms of their sleep quality, easing their symptoms and promoting healing.

Incorporation by Reference

For all purposes, each and every publication and patent document cited in this disclosure is hereby incorporated herein by reference in its entirety for all purposes to the same extent as if each such publication or document was explicitly and individually indicated to be incorporated herein by reference.

Although the technology described above is illustrated in part by compositions referred to by the names Purzorb®, Hempzorb81 and Med 7, the claimed invention is not limited except with respect to the features that are explicitly referred to or otherwise required. Theories that are put forth in this disclosure in terms of the underlying mode of action of various products and components are provided for the interest and possible edification of the reader, and do not limit practice of the claimed invention. With respect to the preparation of cannabinoids from hemp oil and their use, the description is not limiting. The reader may use the technology put forth in this disclosure for any suitable purpose.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed and their equivalents.

The invention claimed is:

1. A therapeutic preparation of full spectrum hemp oil formulated for oral administration to a human subject,
   comprising 0.1% cannabinoids as a percent by weight of the preparation;
   wherein at least 80% of the cannabinoids in the preparation are in the form of micelles suspended in an aqueous solvent;
   wherein the cannabinoids comprise the following: at least 70% cannabidiol (CBD), at least 2% tetrahydrocannabivarin (THCV), at least 5% cannabidivarin (CBDV), and less than 1% Δ9-tetrahydrocannabinol (THC) as a percent by weight of the cannabinoids in the preparation;
   wherein the micelles in the preparation have a median diameter between 10 and 100 nm;
   wherein the micelles in the preparation are sized and formulated to promote intestinal absorption of the cannabinoids into the subject, whereby 25% to 50% or more of the cannabinoids from the preparation reach the circulation within 6 hours of oral administration.

2. The therapeutic preparation of claim 1, further comprising 1% cinnamon oil and/or 1% clove oil as a percent by weight of the preparation.

3. The therapeutic preparation of claim 1, wherein the micelles contain in the micelle's outer surface an amphipathic molecule which is one of the following: polyethylene glycol (PEG) 40 hydrogenated castor oil, polyethylene glycol-phosphatidylethanolamine (PEG-PE), poly(N-vinyl pyrrolidone) (PVP). poly(N-isopropylacrylamide) (pNIPAM), poloxamer 407, poloxamer 188, poloxamer 85, and tocopherol methoxypolyethylene glycol succinate (TPGS); or a combination of two or more thereof.

4. The therapeutic preparation of claim 1, which has both an onset of action and a potency that is at least 4 times better than a standard preparation of CBD oil due to an increase in the rate of absorption into the circulation.

5. The therapeutic preparation according to claim 1 that comprises amounts of each of said cannabinoids formulated to be effective in lowering average blood glucose level and/or treating Type II diabetes in a subject in need thereof.

6. The therapeutic preparation according to claim 1 that comprises amounts of each of said cannabinoids formulated to be effective in decreasing joint pain, decreasing circulating TNF and IL-6 levels, and improving HDL/LDL ratio in a subject in need thereof.

7. The therapeutic preparation according to claim 1 that comprises amounts of each of said cannabinoids formulated to be effective in increasing the amount of a night's sleep of a subject that is spent in deep sleep by at least 30 minutes.

8. The therapeutic preparation according to claim 7, which further comprises extracts of valerian and/or skullcap.

9. A method of preparing a therapeutic preparation according to claim 1, comprising:
   dissolving a full-spectrum hemp oil in a water miscible organic solvent to form a solution, wherein the full-spectrum hemp oil comprises cannabinoids and fatty acids, wherein the cannabinoids contain the following: at least 70% cannabidiol (CBD), at least 2% tetrahydrocannabivarin (THCV), at least 5% cannabidivarin (CBDV), and less than 1% Δ9-tetrahydrocannabinol (THC) as a percent weight of cannabinoids in the hemp oil;

mixing or injecting the solution into an aqueous suspension of micelles into said therapeutic preparation;

wherein the hemp oil, the water miscible organic solvent, the aqueous environment, and the mode of mixing or injecting are selected and adjusted such that at least 80% by weight of the cannabinoids in the aqueous suspension is in the form of micelles having a median diameter between 10 nm and 100 nm.

10. A method of treating inflammation or joint pain in a human subject, the method comprising administering the therapeutic preparation of claim 1 to the subject periodically or every day for at least 20 days.

11. A method of treating a sleep disturbance or improving sleep quality in a human subject, the method comprising administering the therapeutic preparation of claim 1 to the subject periodically or every day for at least 20 days.

\* \* \* \* \*